(12) United States Patent
Ishizaki

(10) Patent No.: US 8,628,561 B2
(45) Date of Patent: Jan. 14, 2014

(54) WATER-ABSORBENT PAD

(75) Inventor: Shingo Ishizaki, Kashiba (JP)

(73) Assignee: Ishizaki Shizai Co. Ltd., Kashiwara-Shi, Osaka (JP)

( * ) Notice: Subject to any disclaimer, the term of this patent is extended or adjusted under 35 U.S.C. 154(b) by 337 days.

(21) Appl. No.: 13/263,186

(22) PCT Filed: Feb. 12, 2010

(86) PCT No.: PCT/JP2010/052057
§ 371 (c)(1),
(2), (4) Date: Oct. 6, 2011

(87) PCT Pub. No.: WO2010/119719
PCT Pub. Date: Oct. 21, 2010

(65) Prior Publication Data
US 2012/0046720 A1 Feb. 23, 2012

(30) Foreign Application Priority Data
Apr. 15, 2009 (JP) ................ 2009-099283

(51) Int. Cl.
*A61F 7/00* (2006.01)
(52) U.S. Cl.
USPC ........................................ 607/114
(58) Field of Classification Search
USPC ........................................ 607/114
See application file for complete search history.

(56) References Cited

U.S. PATENT DOCUMENTS

| 5,376,392 A * | 12/1994 | Ikegami et al. ............ 426/127 |
| 5,709,089 A * | 1/1998 | Dawson et al. ................ 62/4 |
| 7,047,970 B2 * | 5/2006 | Umeda et al. .......... 128/206.21 |

(Continued)

FOREIGN PATENT DOCUMENTS

| JP | 4-25718 U | 2/1992 |
| JP | 11-061501 A | 3/1999 |
| WO | WO 2006/109545 A1 | 10/2006 |

OTHER PUBLICATIONS

International Search Report (PCT/ISA/210) issued on Mar. 23, 2010, by Japanese Patent Office as the International Searching Authority for International Application No. PCT/JP2010/052057.

(Continued)

*Primary Examiner* — Linda Dvorak
*Assistant Examiner* — Kaitlyn Smith
(74) *Attorney, Agent, or Firm* — Buchanan Ingersoll & Rooney PC

(57) ABSTRACT

It is an object of the present invention to provide a water-absorbent pad that is made of impermeable cloth or sheet, that is capable of absorbing water when needed and that effectively cools and heats a human face, neck, head and the like. A cooling/heating water-absorbent pad, wherein a water-absorbent sheet made of a material containing water-absorbent polymer is inserted in a planate bag made of impermeable cloth having a closed periphery; the impermeable cloth and the water-absorbent sheet are stitched together such that the impermeable cloth and the water-absorbent sheet are divided into a plurality of areas in a planar view; and water is absorbed into the water-absorbent sheet through a channel formed at the stitched portion. In this moment, water is absorbed into the water-absorbent sheet only via holes made by the stitching and by a capillary action of a thread piercing through the water-absorbent sheet. The water-absorbent sheet is preferably made of non-woven cloth containing water-absorbent polymer. The impermeable cloth may have a water-repellent surface.

7 Claims, 4 Drawing Sheets

(56) References Cited

U.S. PATENT DOCUMENTS

| | | | |
|---|---|---|---|
| 7,243,509 B2 * | 7/2007 | Trinh et al. | 62/457.2 |
| 7,387,205 B1 * | 6/2008 | Wilson | 206/524.4 |
| 8,261,734 B2 * | 9/2012 | Dodo | 126/204 |
| 2001/0042546 A1 * | 11/2001 | Umeda et al. | 128/206.21 |
| 2002/0017310 A1 * | 2/2002 | Gruenbacher et al. | 132/320 |
| 2006/0010902 A1 * | 1/2006 | Trinh et al. | 62/457.2 |
| 2009/0000610 A1 * | 1/2009 | Dodo | 126/263.01 |
| 2009/0049578 A1 | 2/2009 | Toyohiro | |

OTHER PUBLICATIONS

Written Opinion (PCT/ISA/237) issued on Mar. 23, 2010, by Japanese Patent Office as the International Searching Authority for International Application No. PCT/JP2010/052057.

* cited by examiner (A)

(B)

(A)

(B)

WATER-ABSORBENT PAD

TECHNICAL FIELD

The present invention relates to a water-absorbent pad, and more particularly to a water-absorbent pad for cooling and heating a human face, neck, head and the like.

BACKGROUND ART

Various kinds of water-absorbent pads made of water-absorbent sheet for effectively cooling and heating a human face, neck, head and the like have been provided and proposed. Conventionally, there have been such water-absorbent pads made of permeable cloth or impermeable sheet.

With respect to a pad made of permeable cloth, the pad is caused to absorb water only when it is used, and the pad is convenient for storage. However, while the pad is used, water leaks from the pad through the cloth, whereby the user gets his/her skin and/or clothes wet. With respect to a pad made of impermeable sheet, water is absorbed in the pad during the production process, and therefore, the pad is heavy and big, which is inconvenient for storage. Thus, pads that are made of impermeable cloth or sheet and that absorb water when needed have not been known.

In the field of water-absorbent pad, prior art search was made via Property Company to search for patent documents disclosing that water is absorbed in and exuded from water-absorbent polymer covered with an impermeable cloth or sheet. As a result, such patent documents were not found.

SUMMARY OF THE INVENTION

Objects of the Invention

An object of the present invention is to provide a water-absorbent pad for effectively cooling and heating a human face, neck, head and the like, the pad being made of impermeable cloth or sheet and absorbing water when needed.

Means for Attaining the Objects

In order to attain the object, a cooling/heating water-absorbent pad according to an embodiment of the present invention is characterized in that: a water-absorbent sheet made of a material containing water-absorbent polymer is inserted in a planate bag made of impermeable cloth or sheet having a closed periphery; the impermeable cloth or sheet and the water-absorbent sheet are stitched together such that the impermeable cloth or sheet and the water-absorbent sheet are divided into a plurality of areas in a planar view; and water is absorbed into the water-absorbent sheet only via holes made by the stitching and by a capillary action of a thread piercing through the water-absorbent sheet.

When the water-absorbent pad is soaked in water, the water is absorbed into the water-absorbent sheet through a channel formed at the stitched portion. More specifically, the water penetrates into the water-absorbent sheet via holes made by the stitching and by a capillary action of the thread piercing through the water-absorbent sheet. The pad with water absorbed therein is cooled in a refrigerator or heated by a heater, and the cooled or heated pad is put on a human face or is wound around a human neck or head. In this way, the water-absorbent pad exerts a cooling effect or a heating effect. When the water-absorbent pad is used for cooling, vaporization heat caused by water evaporation through the channel (the thread and the holes at the stitched portions) works synergistically.

When the water-absorbent pad absorbs water, the water-absorbent sheet swells. In this state, the stitched portion serves as not only a channel but also a thickness adjuster for preventing the water absorbed in an area of the water-absorbent polymer from moving to other areas and for adjusting the swelling in the thickness direction. The water-absorbent sheet swells in the thickness direction, and thereby, the water-absorbent pad retains water more than a specified amount and can maintain a desired temperature for a specified time.

The surface of the water-absorbent pad is made of impermeable cloth or sheet, and the user of the water-absorbent pad does not get his/her skin and/or clothes wet. When the water-absorbent sheet absorbs water and gets in the swelling state, the stitched portion become a dent and is hidden as a trough between bulging portions. In this state, although water leaks out through the holes and the thread at the stitched portion, the water does not adhere to the user's skin and/or clothes, and the user does not get his/her skin and/or clothes wet. This is because the stitched portion is in the trough.

While the water-absorbent pad does not retain water, the pad is light and can be folded up or wound up in a compact form.

Non-woven cloth containing water-absorbent polymer is suited to be used as the water-absorbent sheet. Also, it is preferable that the impermeable cloth or sheet has a water-repellent surface.

Effects of the Invention

A water-absorbent pad according to the present invention is made of impermeable cloth or sheet and is capable of absorbing water when needed, and the pad effectively cools and heats a human face, neck, head and the like. Further, the pad does not cause the user to get his/her skin and/or clothes wet.

MODES FOR CARRYING OUT THE INVENTION

Water-absorbent pads according to some embodiments of the present invention will be hereinafter described with reference to the accompanying drawings.

First Embodiment; See FIGS. 1-4

Figure 1:
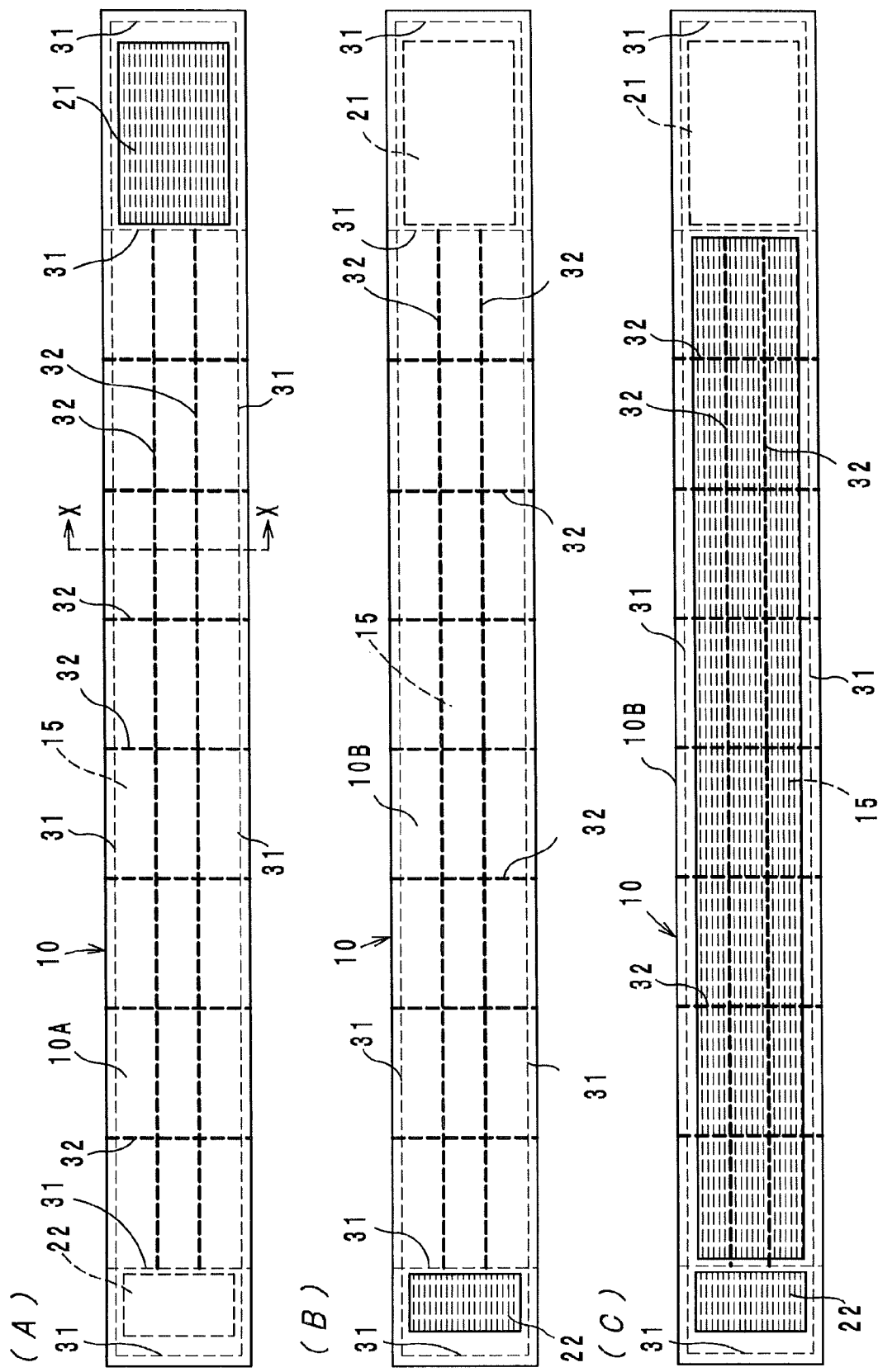
FIG. 1 shows a water-absorbent pad according to a first embodiment of the invention, (A) being a top view, (B) being a bottom view and (C) being a bottom view showing the location of a water-absorbent sheet.
Figure 2:
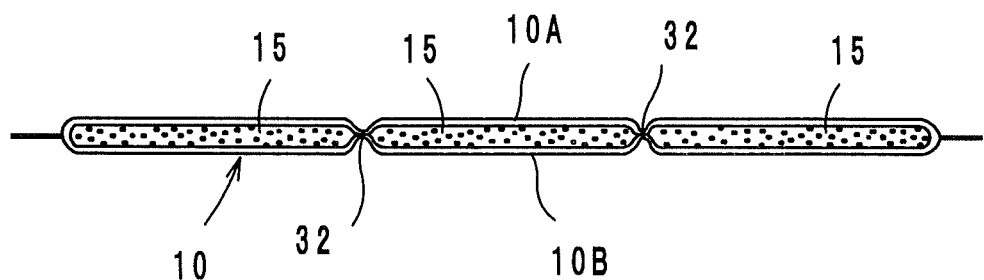
FIG. 2 is a cross-sectional view of the water-absorbent pad along the line X-X shown in FIG. 1(A), (A) showing a state before absorbing water and (B) showing a state after absorbing water.
Figure 2:
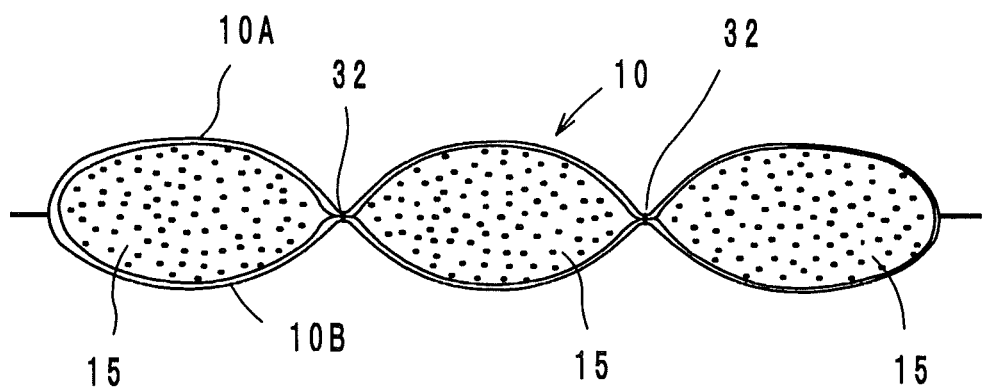

As shown by FIG. 1, a water-absorbent pad according to a first embodiment of the present invention has a water-absorbent sheet 15 made of a material containing water-absorbent polymer in a planate impermeable cloth bag 10 having a closed periphery. More specifically, the bag 10 is formed of two cuts of impermeable cloth (a front cloth 10A and a back cloth 10B) that are brought together by closure at the periphery, and the water-absorbent sheet 15 is tucked in the bag 10. The impermeable cloths 10A and 10B and the water-absorbent sheet 15 are stitched together with a sewing machine such that the cloths 10A, 10B and the sheet 15 are divided into a plurality of areas in a planar view.

Figure 3:
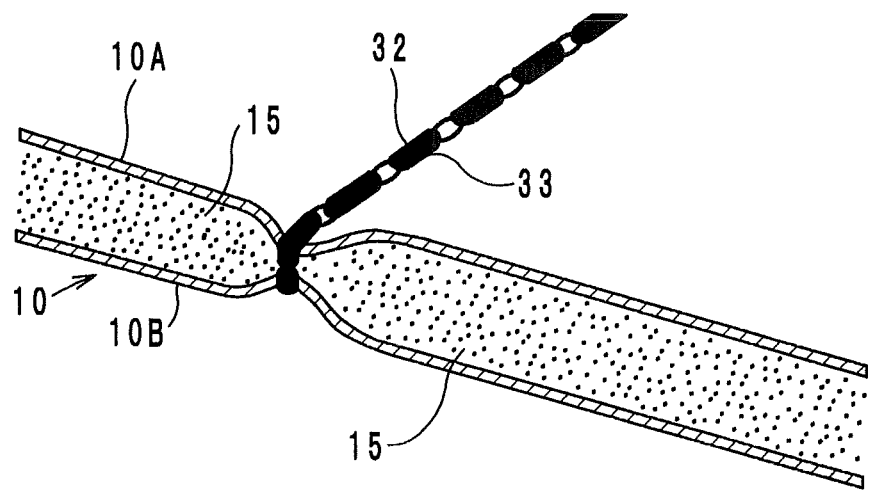
FIG. 3 is a perspective view of a stitched portion of the water-absorbent pad according to the first embodiment.
Figure 4:
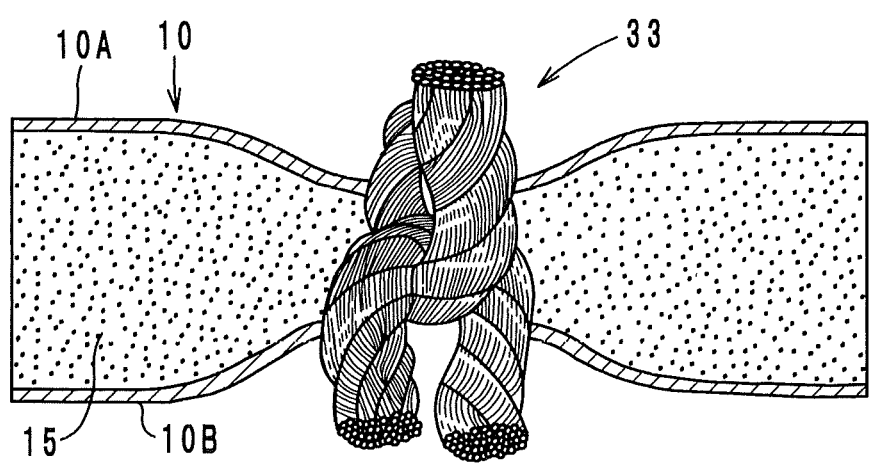
FIG. 4 is an enlarged view of a part of the perspective view of FIG. 3.

On a front side (shown by FIG. 1(A)) of the pad, at the right end, a fastener tape 21 is attached, and on a back side (shown by FIG. 1(B) of the pad, at the left end, a fastener tape 22 is attached. The front cloth 10A and the back cloth 10B are sewed together at dotted lines 31 in FIG. 1, whereby the cloths 10A and 10B are formed into a bag 10. The cloths 10A, 10B and the sheet 15 are stitched together at dotted lines 32. FIGS. 3 and 4 are enlarged views of a cross section of a stitched portion. The number 33 denotes a thread used for the stitching.

Non-woven cloth containing water-absorbent polymer is suited to be used for the water-absorbent sheet 15. The water-absorbent polymer is a well-known material, and non-woven cloth containing water-absorbent polymer is off-the-shelf. However, other materials as well as non-woven cloth can be used for the water-absorbent sheet 15.

When the water-absorbent pad of the above structure is soaked in water, the water penetrates into the water-absorbent polymer inside the pad through channels formed of the threads and holes at the stitched portions by capillarity. In this moment, because the threads 33 and the holes at the stitched portions are directly in contact with the water-absorbent sheet 15, the water absorption is efficient.

The water-absorbent pad with water absorbed therein is cooled in a refrigerator, and the cooled pad is put on a human face or is wound around a human neck or head with the fastener tapes 21 and 22 joined together. In this way, the water-absorbent pad exerts a cooling effect. Also, vaporization heat caused by water evaporation through the threads 33 and the holes at the stitched portions works synergistically. On the other hand, the water-absorbent pad with water absorbed therein may be heated, and in this case, the pad can be used as a pad having a heating effect.

Water evaporates naturally from the channels, and the water-absorbent pad returns to a dry state. The water-absorbent pad in the dry state is substantially flat as shown by FIG. 2(A) and light, and it is possible to fold up or wind up the pad into a compact form. When the water-absorbent pad absorbs water, the water-absorbent sheet 15 absorbs water and swells as shown by FIG. 2(B). In this state, the pad can be bent at the stitched portions 32 and wound around a human body.

The stitched portions 32 serve not only as channels but also thickness adjusters for preventing the water absorbed in each area of the water-absorbent polymer from moving to other areas and for adjusting the swelling in the thickness direction. The water-absorbent sheet 15 swells in the thickness direction, and thereby, the water-absorbent pad retains water more than a specified amount and can maintain a desired temperature for a specified time. When the water-absorbent sheet 15 is in the swelling state, the stitched portions 32 become dents and are hidden as troughs among bulging portions. In other words, when the divided areas of the water-absorbent pad absorb water and swell, in a cross-sectional view of the water-absorbent pad, the stitched portions 32 (serving as channels) are located at the intersections of "X"s. In this state, although water seeks from the swelling areas to the stitched portions 32 (to the channels) through the holes and the threads 33, the water seeking to the channels does not adhere to the user's skin and/or clothes, and the user does not get his/her skin and/or clothes wet. This is because the channels are in the troughs.

The surface of the water-absorbent pad is made of impermeable cloth (10A, 10B), and the user of the water-absorbent pad does not get his/her skin and/or clothes wet. In order to achieve a good effect of vaporization heat, it is preferable that the surface of the water-absorbent pad is made of cloth that is breathable as well as impermeable. Also, the impermeable surface cloths 10A and 10B are preferably water-repellent cloths. Further, the water-absorbent pad may be entirely antibacterial, deodorant and/or antifouling.

Second Embodiment; See FIGS. 5 and 6

Figure 5:
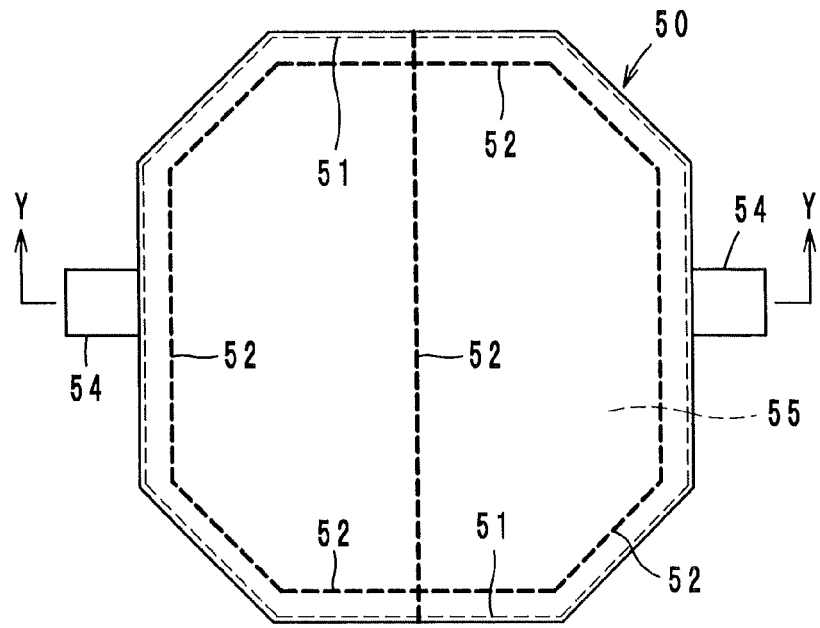
FIG. 5 shows a water-absorbent pad according to a second embodiment of the present invention, (A) being a top view and (B) being a cross-sectional view along the line Y-Y shown in (A)

A water-absorbent pad according to a second embodiment of the present invention can be used as a hot-water bag. As shown by FIG. 5, the water-absorbent pad according to the second embodiment has a water-absorbent sheet 55 made of a material containing water-absorbent polymer in an impermeable cloth bag 50 having a closed periphery. More specifically, the bag 50 is formed of two octagonal cuts of cloth (a front cloth 50A and a back cloth 50B) that are brought together by closure at the periphery, and the water-absorbent sheet 55 is tucked in the bag 50. The impermeable cloths 50A and 50B and the water-absorbent sheet 55 are stitched together with a sewing machine such that the cloths 50A, 50B and the sheet 55 are divided into a plurality of areas in a planar view. Further, cloth flaps 54 are sewed to the bag 50 at the right and left sides.

The front cloth 50A and the back cloth 50B are sewed together at dotted lines 51, whereby the cloths 50A and 50B are formed into a bag 50. The cloths 50A, 50B and the sheet 55 are stitched at dotted lines 52. A cross section of a stitched portion is shown by the enlarged views of FIGS. 3 and 4. The water-absorbent sheet 55 is made of the same material as the water-absorbent sheet 15 is.

Figure 6:
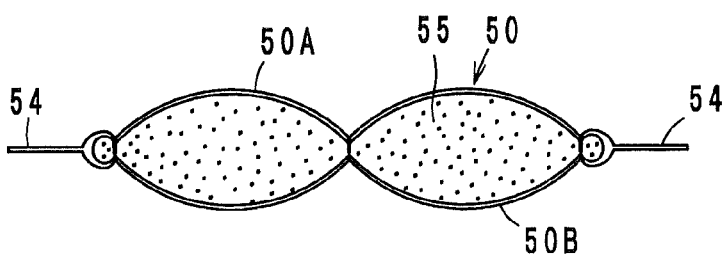
FIG. 6 is a cross-sectional view of the water-absorbent pad according to the second embodiment showing a state after absorbing water.

When the water-absorbent pad of the above structure is soaked in water, the water penetrates into the water-absorbent polymer inside the pad through channels formed of the threads and holes at the stitched portions by capillarity. In this moment, because the threads at the stitched portions are directly in contact with the water-absorbent sheet 15, the water absorption is efficient. FIG. 6 shows the state after the water absorption.

The water-absorbent pad with water absorbed therein is heated in a microwave range, and the heated pad can be used as a hot-water bag. The function effect of the second embodiment is the same as that of the first embodiment. Further, since the water-absorbent pad naturally evaporates water, while the water-absorbent pad is used as a hot-water bag in a bed, the inside of the bed does not become too dry. The flaps 54 do not heat up although the water-absorbent pad is heated in a microwave range, and therefore the user can brings out the pad (hot-water bag) from the microwave range easily.

Other Embodiments

The present invention is not limited to be implemented as the water-absorbent pad according to the embodiments above, and various changes and modifications are possible within the scope of the invention. Especially, as the surface of the pad, an impermeable sheet instead of the impermeable cloth may be used.

INDUSTRIAL APPLICABILITY

As described above, the present invention is applicable effectively to a water-absorbent cooling and/or heating pad. A water-absorbent pad according to the present invention has the advantages of absorbing water when needed, of effectively cooling or heating a human face, neck, head and the like and of not causing the user to get his/her skin and/or clothes wet.

DESCRIPTION OF THE REFERENCE SYMBOLS

10, 50: bag
10A, 10B, 50A, 50B: impermeable cloth
15, 55: water-absorbent sheet
32, 52: stitched portion
33: thread

The invention claimed is:

1. A cooling/heating water-absorbent pad, wherein:
a water-absorbent sheet made of a material containing water-absorbent polymer is inserted in a planate bag made of impermeable cloth or sheet having a closed periphery;
the impermeable cloth or sheet and the water-absorbent sheet are stitched together such that the impermeable cloth or sheet and the water-absorbent sheet are divided into a plurality of areas in a planar view; and
water is absorbed into the water-absorbent sheet only via holes made by the stitching and by a capillarity action of a thread piercing through the water-absorbent sheet.

2. A cooling/heating water-absorbent pad according to claim 1, wherein when the water-absorbent sheet absorbs water, which makes the divided areas swell, a portion at which the impermeable cloth or sheet and the water-absorbent sheet are stitched together becomes a dent and is hidden.

3. A cooling/heating water-absorbent pad according to claim 2, wherein the water-absorbent sheet is made of nonwoven cloth containing water-absorbent polymer.

4. A cooling/heating water-absorbent pad according to claim 2, wherein the impermeable cloth or sheet has a water-repellent surface.

5. A cooling/heating water-absorbent pad according to claim 1, wherein the water-absorbent sheet is made of nonwoven cloth containing water-absorbent polymer.

6. A cooling/heating water-absorbent pad according to claim 5, wherein the impermeable cloth or sheet has a water-repellent surface.

7. A cooling/heating water-absorbent pad according to claim 1, wherein the impermeable cloth or sheet has a water-repellent surface.

* * * * *